(12) United States Patent
Egry et al.

(10) Patent No.: US 10,401,366 B2
(45) Date of Patent: Sep. 3, 2019

(54) PROTEIN MELT ANALYSIS USING DIPYRROMETHENEBORON DIFLUORIDE COMPOUNDS

(71) Applicant: LIFE TECHNOLOGIES CORPORATION, Carlsbad, CA (US)

(72) Inventors: Levente Egry, Sunnyvale, CA (US); Kyle Gee, Springfield, OR (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 15/392,295

(22) Filed: Dec. 28, 2016

(65) Prior Publication Data

US 2017/0160284 A1 Jun. 8, 2017

Related U.S. Application Data

(62) Division of application No. 13/751,030, filed on Jan. 25, 2013, now Pat. No. 9,568,478.

(60) Provisional application No. 61/591,383, filed on Jan. 27, 2012.

(51) Int. Cl.
| | |
|---|---|
| *G01N 33/68* | (2006.01) |
| *C07F 5/02* | (2006.01) |
| *G01N 33/58* | (2006.01) |
| *C09B 57/00* | (2006.01) |
| *G01N 33/52* | (2006.01) |
| *C09B 23/04* | (2006.01) |

(52) U.S. Cl.
CPC ......... *G01N 33/6803* (2013.01); *C07F 5/022* (2013.01); *C09B 23/04* (2013.01); *C09B 57/00* (2013.01); *G01N 33/52* (2013.01); *G01N 33/582* (2013.01); *G01N 33/68* (2013.01)

(58) Field of Classification Search
CPC ...................................................... C07F 5/022
See application file for complete search history.

(56) References Cited

U.S. PATENT DOCUMENTS

| | | | |
|---|---|---|---|
| 7,897,787 B2 | 3/2011 | Matsumoto et al. | |
| 2009/0035868 A1* | 2/2009 | Diller | G01N 33/582 436/86 |

FOREIGN PATENT DOCUMENTS

WO    1999/024050 A1    5/1999

OTHER PUBLICATIONS

Matsumoto, T. et al. "A Thiol-Reactive Fluorescence Probe Based on Donor-Excited Photoinduced Electron Transfer: Key Role of Ortho Substitution," Org. Lett., 2007, 9 (17), pp. 3375-3377.*
Volkmer: T. et al."Assembly of a transmembrane b-Type cytochrome is mainly driven by transmembrane helix interactions," Biochimica et Biophysica Acta (BBA)—Biomembranes vol. 1758, Issue 11, Nov. 2006, pp. 1815-1822.*

(Continued)

*Primary Examiner* — Christopher Adam Hixson
*Assistant Examiner* — Michelle Adams

(57) ABSTRACT

According to the present teachings, systems, compositions, kits and methods for protein melt analysis are provided that utilizing a dye that is a dipyrrometheneboron difluoride compound. In some embodiments, a method comprises preparing a sample by mixing at least one protein with a dye, and applying a controlled heating, while recording the fluorescence emission of the sample.

13 Claims, 10 Drawing Sheets

(56) References Cited

OTHER PUBLICATIONS

Wright, W.W. et al. "Protein in Sugar Films and in Glycerol/Water as Examined by Infrared Spectroscopy and by the Fluorescence and Phosphorescence of Tryptophan," Biophysical Journal, vol. 85, Issue 3, Sep. 2003, pp. 1980-1995.*

Bouwstra, J., "The skin barrier in healthy and diseased state (Only Section 2. Stratum corneum lipid composition and organization in normal skin)", Biochemica et Biophisica Acta. vol. 1758, Issue 12, 2006, pp. 2082-2089 (selected section pages only).

Ericsson, et al., "Thermofluor-based high-throughput stability optimization of proteins for structural studies", Analytical Biochemistry, vol. 357, No. 2, Academic Press Inc., New York, Oct. 15, 2006, 289-298.

Matsumoto, et al., "A Thiol-Reactive Fluorescence Probe Based on Donor-Excited Photoinduced Electron Transfer: Key Role of Ortho Substitution", Organic Letters, vol. 9, No. 17, Aug. 1, 2007, pp. 3375-3377, (2007).

Molecular Probes, Thiol-Reactive Probes, Chapter 2, 2010, 47-62.

PCT/US2013/023321, International Search Report and Written Opinion dated May 14, 2013, 11 pages.

Sandros, et al., "General, high-affinity approach for the synthesis of fluorophore appended protein nanoparticle assemblies", Chemical Communications, No. 22, Jan. 1, 2005, pp. 2832-2834.

Volkmer, T., et al., "Assembly of a Transmembrane b-Type Cytochrome is mainly driven by transmembrane helix interactions", Biochimica et Biophysica Acta—Biomembranes; vol. 1758, Issue 11, Nov. 2006, 1815-1822.

Wallgren, et al., "Extreme Temperature Tolerance of a Hyperthermophilic Protein Coupled to Residual Structure in the Unfolded State", Journal of Molecular Biology, vol. 379, No. 4, Jun. 1, 2008, pp. 845-858.

Wright, W. W., et al., "Protein in Sugar Films and in Glycerol/Water as Examined by Infrared Spectroscopy and by the Fluorescence and Phosphorescence of Tryptophan", Biophysical Journal, Sep. 2003; 85(3): 1980-1995.

Extended European Search Report for Application No. 18198082.2 dated Mar. 14, 2019, 7 pages.

* cited by examiner

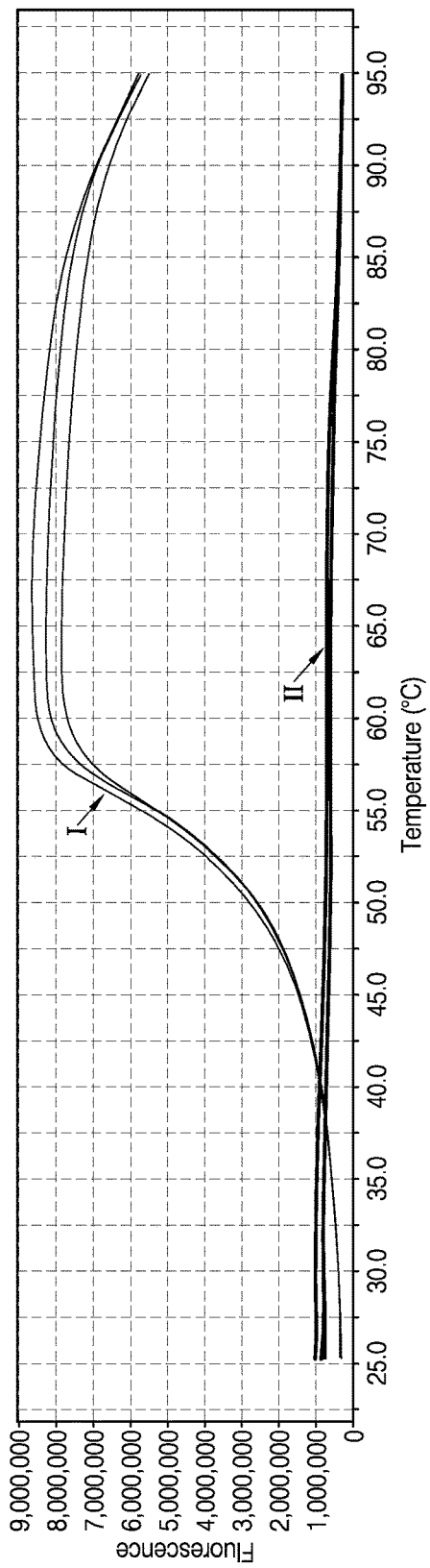
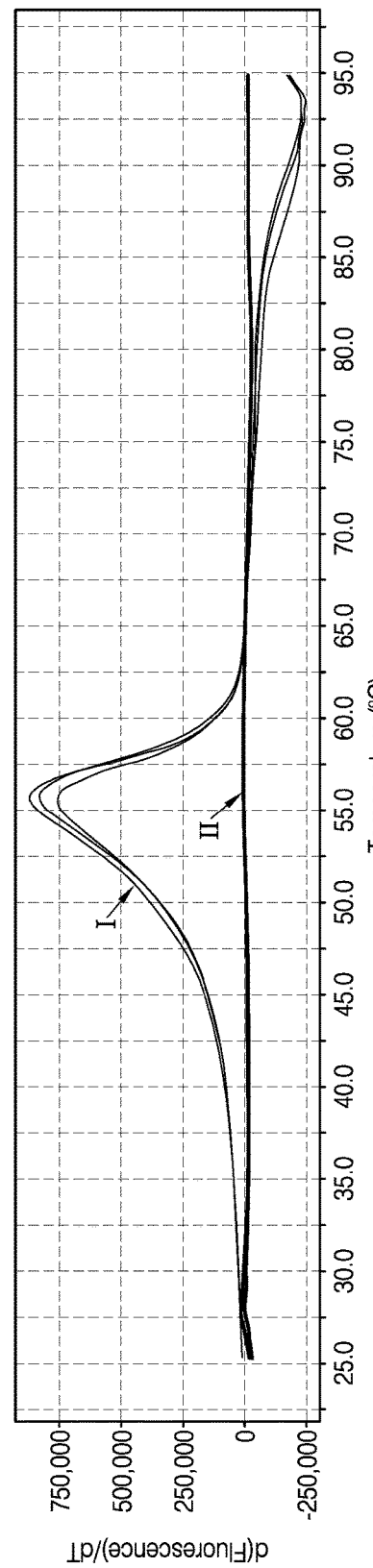
FIG. 3A
FIG. 3B

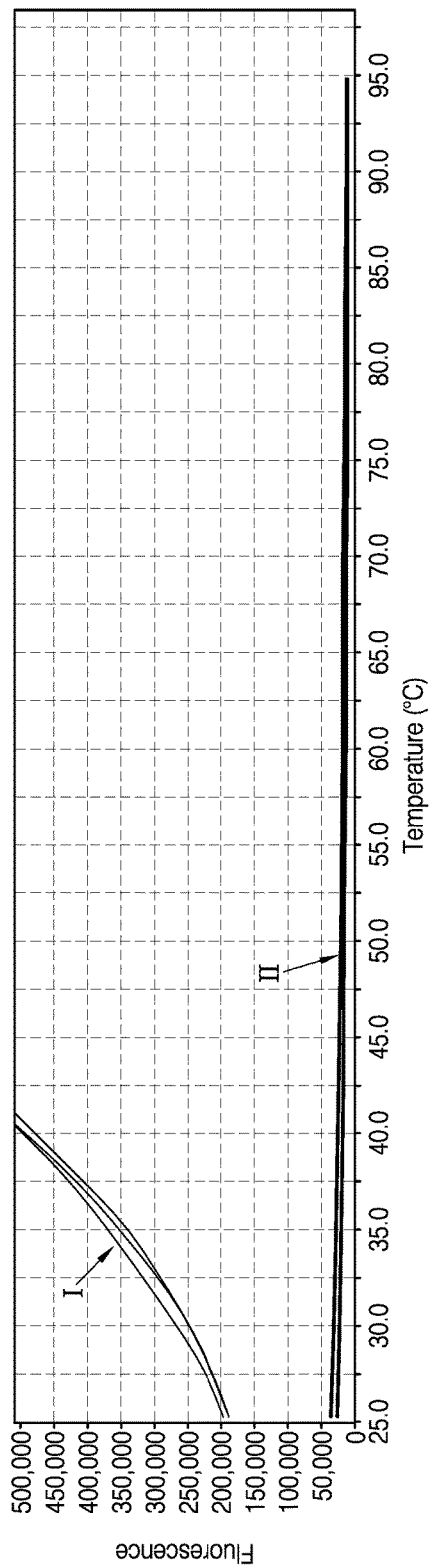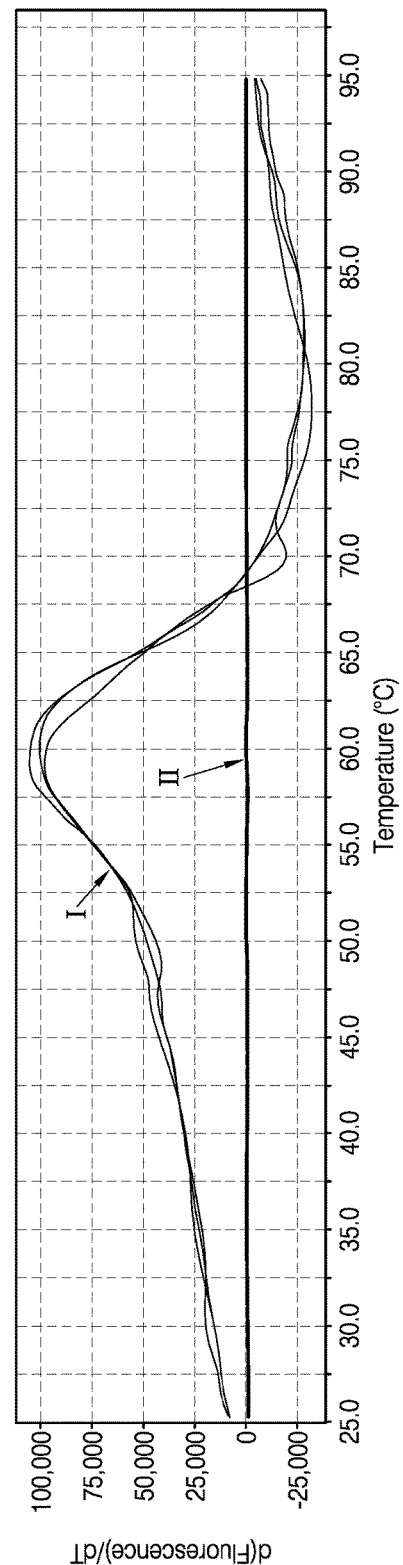
FIG. 6A
FIG. 6B

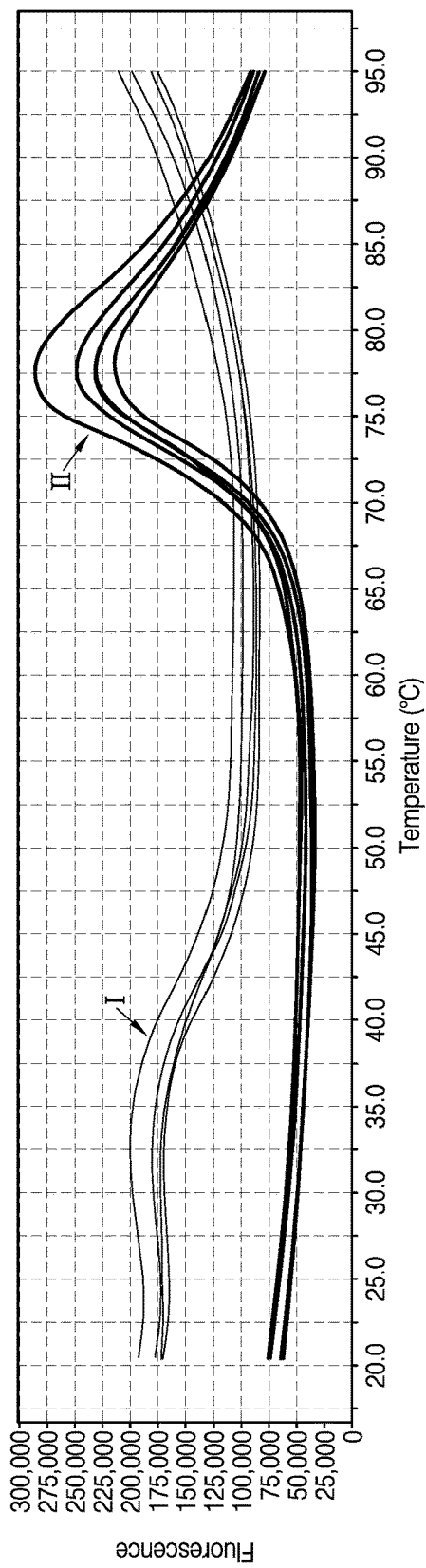
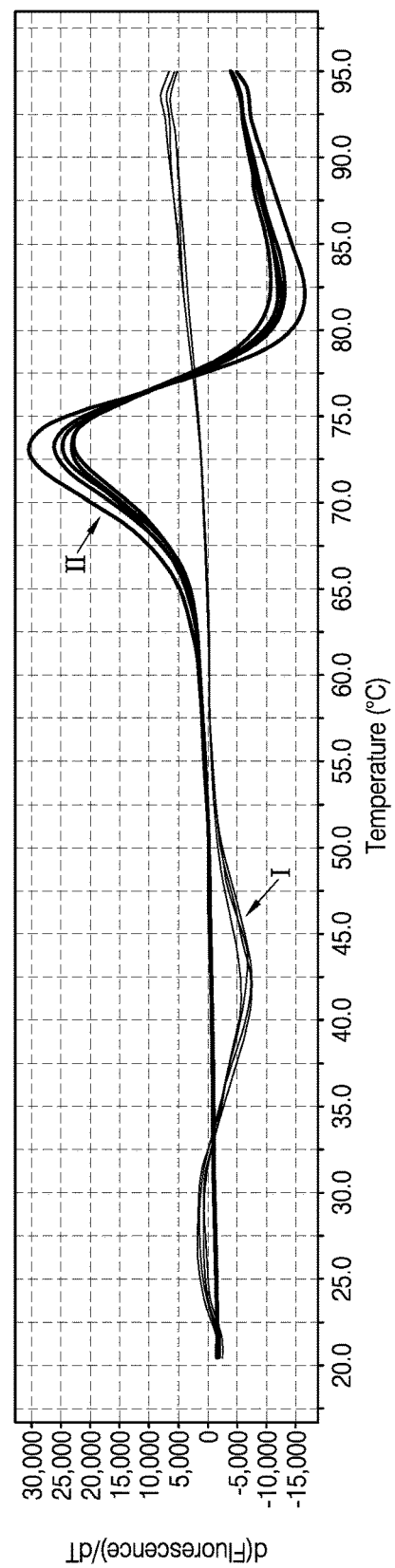
FIG. 9A
FIG. 9B

PROTEIN MELT ANALYSIS USING DIPYRROMETHENEBORON DIFLUORIDE COMPOUNDS

CROSS-REFERENCE TO RELATED APPLICATIONS

This application is a divisional of U.S. application Ser. No. 13/751,030 filed Jan. 25, 2013, which claims a priority benefit under 35 U.S.C. § 119 (e) to U.S. Provisional App. No. 61/591,383 filed Jan. 27, 2012, the contents of which are incorporated herein by reference in their entirety.

BACKGROUND

Proteins are typically the key molecule studied as the drug target for drug development generation. High throughput screening of small-molecule and ligand libraries that bind to protein targets is an important part of the process—requiring screening of thousands of small molecules and ligands with a variety of different assays, requiring months of time. Protein targets are challenging to work with due to their susceptibility to degradation and aggregation, so protein stability screening is often an important component of lead generation programs. Protein stability screening, performed using the protein melting method, is employed in other research programs that involve native proteins. Protein melting is an extremely useful screening method for the identification of ligands and/or solution (buffer) conditions that maximally stabilize a protein as part of protein purification, crystallization, and functional characterization.

Historically, the methodologies to perform protein melt screening are either very slow and tedious, analyzing one sample at a time—or if high-throughput, require milligram amounts of protein sample and incur high costs in either reagents, or protein samples, or both. It would be useful to have new and useful systems, methods and reagents to screen proteins, including antibodies, to identify ligands, mutations/modifications, buffer conditions, or other factors that affect their melting temperature (Tm) and relative stability.

SUMMARY OF THE DISCLOSURE

Various embodiments of systems and methods for protein melt analysis according to the present teachings provide for the determination of protein melt temperature ($T_m$) using species of a dye given by the parent structure:

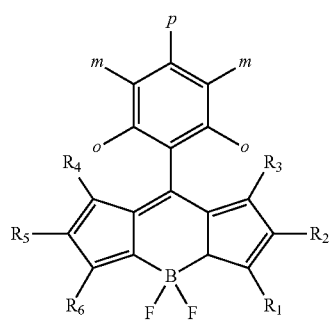

(1)

4,4-difluoro-8-(maleimidylphenyl)-4-bora-3a,4a-diaza-s-indacene wherein:

R1 to R6 may independently be —H, halogen, —$(CH_2)_n$$CO_2H$ (wherein n=0 to 6), —$(CH_2)_n CO_2 R$ (wherein n=0 to 6), cycloakyl, alkyl (1-5 carbons), aryl, heteroaryl, arylalkyl (wherein the alkyl portion is 1-5 carbon atoms), alkenyl, azido, alkynyl, and sulfo; alone or in combination. Substituents o, m and p are independently selected from hydrogen, halogen, —(CH2)nCO2H (wherein n=0 to 6), —(CH2)nCO2R (wherein n=0 to 6), cycloakyl, alkyl (1-5 carbons), aryl, heteroaryl, arylalkyl (wherein the alkyl portion is 1-5 carbon atoms), alkenyl, azido, alkynyl, sulfo, and a maleimidyl substituent having the structure:

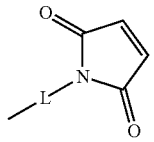

alone or in combination with the provisio that the maleimidyl substituent occurs in formula (I) once and only once. An alkenyl substituent may be substituted or unsubstituted, wherein the alkenyl group is ethenyl, dienyl, or trienyl. Substituents for an alkenyl group may be selected from hydrogen, halogen, alkyl (1-5 carbon atoms), cyano, carboxylate ester, carboxamide, aryl, or heteroaryl. Aryl may be selected from phenyl, 1-naphthyl, 2-naphthyl, 1-pyrenyl, 9-anthryl, pyridyl, quinolyl, and alkoxy derivatives thereof. Any aryl group in any substituent may be further substituted by halogen, —$(CH_2)_n CO_2 H$ (wherein n=0 to 6), —$(CH_2)_n CO_2 R$ (wherein n=0 to 6) alkyl (1-5 carbons), and alkoxy(wherein the alkyl portion is 1-4 carbon atoms). Any alkyl group in any substituent of an aryl group may be further substituted by an ester or amide substituent. L, is an optionally present linker. A linker may be selected from alkyl (1-6 carbons), and heteroalkyl, (1-6 atoms).

Non-limiting examples of a species according to various embodiments of systems and methods may be selected from:

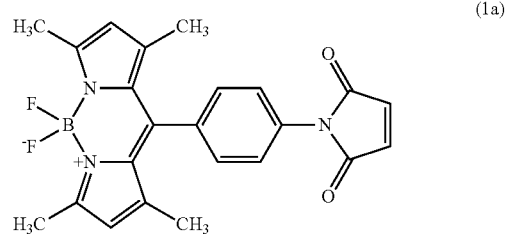

(1a)

4,4-difluoro-1,3,5,7-tetramethyl-8-(4-maleimidylphenyl)-4-bora-3a,4a-diaza-s-indacene (BODIPY® 499/508 maleimide), and from:

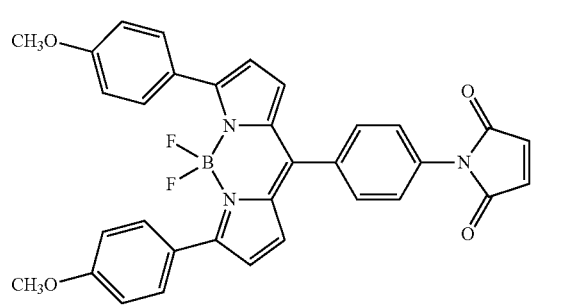

(1b)

4,4-difluoro-3,5-bis(4-methoxyphenyl)-8-(4-maleimidylphenyl)-4-bora-3a,4a-diaza-s-indacene (BODIPY® 577/618 maleimide).

Various embodiments of systems and methods of the present teachings utilize various embodiments of a dye of formula (1) to monitor protein folding. In various systems and methods of the present teachings, a maleimide substituted phenyl ring in position 8 of the dipyrrometheneboron difluoride ring may react selectively with a thiol group of, for example, but not limited by, a naturally occurring cysteine residue in a protein to form a covalent C—S bond between a dipyrrometheneboron difluoride dye species as depicted in formula (1) and the cysteine residue. A protein so selectively modified may then be thermally denatured, so that the dye tag may be used to monitor the progress of the thermal denaturation, and a melting temperature ($T_m$) may then be determined from the data so generated.

According to various embodiments, the stability of the dye and of the dye-thiol bond may provide for a wide variety of assay conditions under which a protein melt analysis may be run, thereby providing for a wide number of types of proteins and types of thermal melt assays that may be performed. For various embodiments of the present teachings, a species of a dye of formula (1) may be selected so that it has an excitation wavelength of between about 470 nm to about 650 nm, and an emission wavelength between about 500 nm to about 700 nm. As one of ordinary skill in the art is apprised, proteins may be damaged by irradiation in the UV. Therefore, for the purpose of protein folding study, a dye selected having such excitation/emission characteristics may be advantageous for preserving a protein structure, and therefore providing a consistent protein melt determination. Various embodiments of a dye selected from formula (1) may exhibit enhanced stability towards photobleaching, providing for stable signals solely related to the protein folding process over an entire protein melt analysis. For various embodiments of systems and methods of the present teachings, the thiol group may be an intrinsic feature of a cysteine-containing protein. In various embodiments of systems and methods of the present teachings, a protein or proteins may be specifically tagged with at thiol group to provide for reactivity with a dye selected from formula (1). According to various embodiments, the selectivity of the binding of the dye to cysteine residues in a protein may be useful for discriminating the progress of reaction for cysteine-containing proteins in a mixture of proteins.

BRIEF DESCRIPTION OF THE DRAWINGS

FIG. 3A is a graph of protein thermal shift (PTS) data for β-lactoglobulin (bovine) using a dye according to various embodiments of systems and methods of the present teachings in comparison to dye known in the art of PTS.

FIG. 3B shows the first derivative graphs of the β-lactoglobulin PTS data shown for FIG. 3A.

FIG. 6A is the graph of PTS data for α-chymotrypsin (bovine) shown in FIG. 5A, which is an expanded view of the details of the background for the dye known in the art of PTS.

FIG. 6B depicts the first derivative graphs of the α-chymotrypsin PTS data shown for FIG. 5A.

FIG. 9A is a graph of PTS data for lysozyme (ovine) using a dye according to various embodiments of systems and methods of the present teachings in comparison to dye known in the art of PTS.

FIG. 9B shows the first derivative graphs of the lysozyme PTS data shown for FIG. 9A.

DETAILED DESCRIPTION

Figure 1:
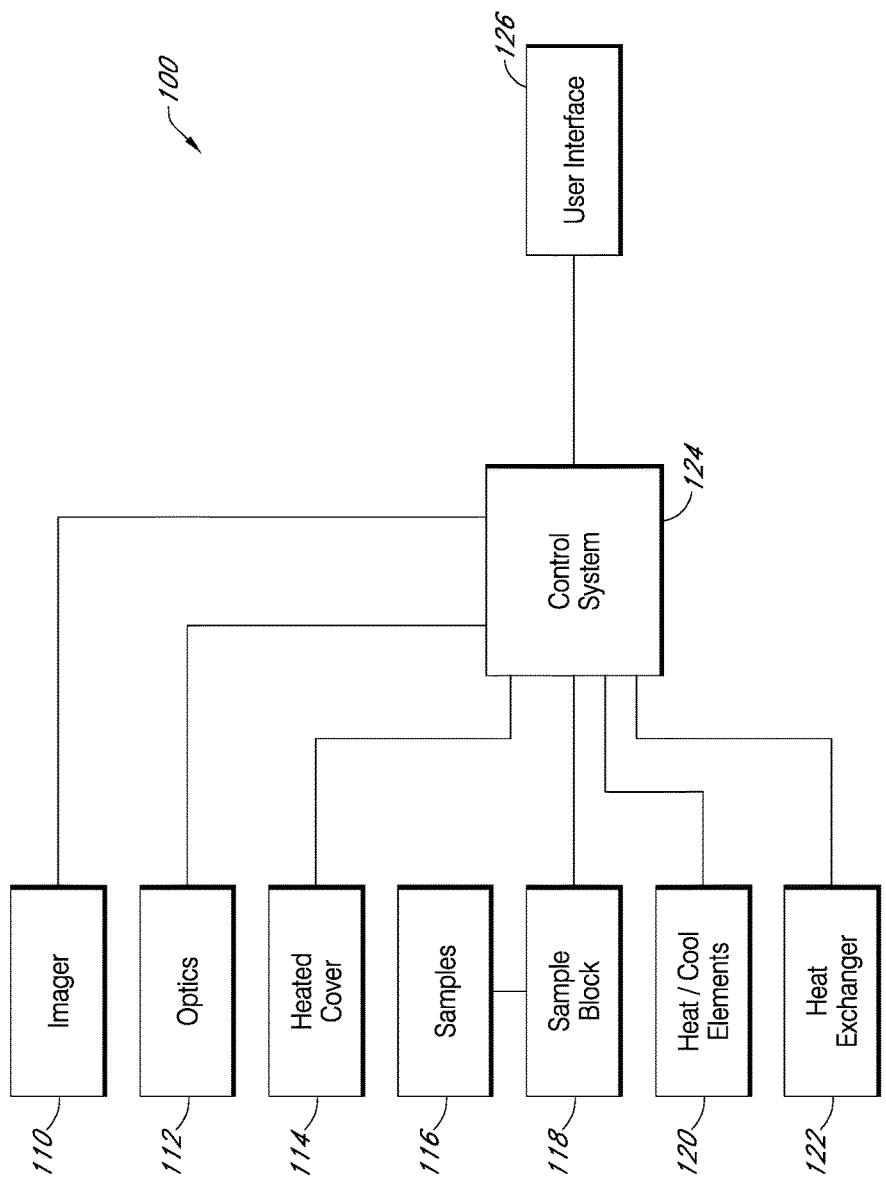
FIG. 1 is a block diagram of a PCR instrument according to various embodiments of methods of the present teachings.

The present teachings relate to embodiments of systems and methods providing for a dye of formula (1) useful for protein melt curve analysis:

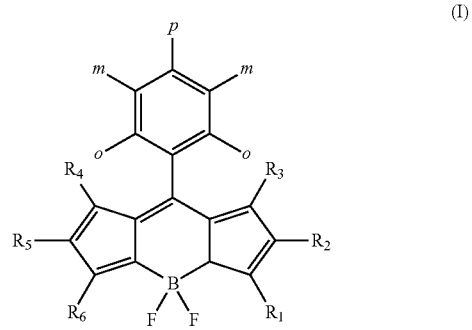

(I)

4,4-difluoro-8-(maleimidylphenyl)-4-bora-3a,4a-diaza-s-indacene wherein:

R1 to R6 may independently be —H, halogen, —(CH$_2$)$_n$CO$_2$H (wherein n=0 to 6), —(CH$_2$)$_n$CO$_2$R (wherein n=0 to 6), cycloakyl, alkyl (1-5 carbons), aryl, heteroaryl, arylalkyl (wherein the alkyl portion is 1-5 carbon atoms), alkenyl, azido, alkynyl, and sulfo; alone or in combination. Substituents o, m and p are independently selected from hydrogen, halogen, —(CH2)$_n$CO2H (wherein n=0 to 6), —(CH2)$_n$CO2R (wherein n=0 to 6), cycloakyl, alkyl (1-5 carbons), aryl, heteroaryl, arylalkyl (wherein the alkyl portion is 1-5 carbon atoms), alkenyl, azido, alkynyl, sulfo, and and a maleimidyl substituent having the structure:

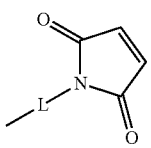

alone or in combination, with the provisio that the maleimidyl substituent occurs in formula (I) once and only once. An alkenyl substituent may be substituted or unsubstituted, wherein the alkenyl group is ethenyl, dienyl, or trienyl. Substituents for an alkenyl group may be selected from hydrogen, halogen, alkyl (1-5 carbon atoms), cyano, carboxylate ester, carboxamide, aryl, or heteroaryl. Aryl may be selected from phenyl, 1-naphthyl, 2-naphthyl, 1-pyrenyl, 9-anthryl, pyridyl, quinolyl, and alkoxy derivatives thereof. Any aryl group in any substituent may be further substituted by halogen, —$(CH_2)_nCO_2H$ (wherein n=0 to 6), —$(CH_2)_n CO_2R$ (wherein n=0 to 6) alkyl (1-5 carbons), and alkoxy (wherein the alkyl portion is 1-4 carbon atoms). Any alkyl group in any substituent of an aryl group may be further substituted by an ester or amide substituent. L, is a linker that is optionally present. According to various embodiments, a linker may be selected from alkyl (1-6 carbons), and heteroalkyl, (1-6 atoms).

According to various embodiments, a melting temperature ($T_m$) may be determined from a protein denaturation study under wide range of assay conditions using various dipyrromethenboron difluoride dyes according to formula (1). In various embodiments of systems and methods according to the present teachings, such a range of assay conditions may include, but not limited by, a wide pH range useful in protein folding studies from about pH 2 to about pH 10, a wide variety of buffer selections and concentrations, and wide variety of other assay constituents, such as various salts of the Hofmeister series, various surfactants, as well as various protein stabilizing agents, such as polysaccharides and other polyols of a wide range of molecular weights and concentrations. According to the present teachings, various dipyrromethenboron difluoride dyes according to formula (1) have excitation wavelengths of between about 470 nm to about 650 nm, and an emission wavelength between about 500 nm to about 700 nm. Accordingly, using dyes selected from formula (1) avoids irradiation of protein samples with UV, thereby avoiding artifacts due to protein photo-degradation. Various embodiments of dipyrromethenboron difluoride dyes according to formula (1) may also exhibit enhanced stability towards photobleaching, providing for stable signals solely related to the protein folding process. Accordingly, dipyrromethenboron difluoride dyes according to formula (1) have attributes that make them useful for a wide variety of protein melt assays.

Non-limiting examples of a species according to various embodiments of systems and methods may be selected from:

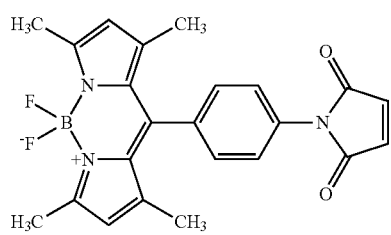

(1a)

4,4-difluoro-1,3,5,7-tetramethyl-8-(4-maleimidylphenyl)-4-bora-3a,4a-diaza-s-indacene (BODIPY® 499/508 maleimide), and from:

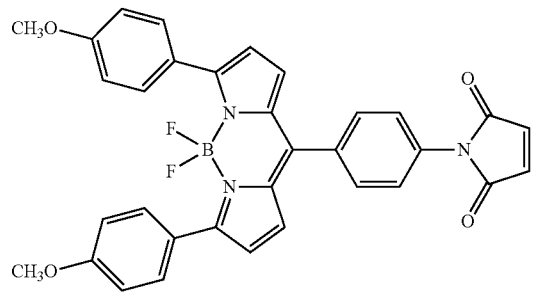

(1b)

4,4-difluoro-3,5-bis(4-methoxyphenyl)-8-(4-maleimidylphenyl)-4-bora-3a,4a-diaza-s-indacene (BODIPY® 577/618 maleimide)

As used herein, "substituted" refers to a molecule wherein one or more hydrogen atoms are replaced with one or more non-hydrogen atoms, functional groups or moieties. For example an exemplary unsubstituted ethenyl group may be represented —CH=CH—. Substituted ethenyl groups may include, for example, but are not limited by, —CH=CH—COOH, —CH=CHCOOR, —CH=CH-Aryl and —CH=CH-Aryl-OR where, for example, R is alkyl or substituted alkyl. As one of ordinary skill in the art is apprised, for a variety of organic dye molecules, some non-limiting exemplary substituents include, hydrogen, halogen alkyl, cycloalkyl, branched alkyl, alkene, cyclic alkene, branched alkene, alkyne, branched alkyne, carboxyl, ester, sulfate, sulfonate, sulfone, amino, ammonium, amido, nitrile, alkoxy, phenoxy, phenyl, polycyclic aromatic, and electron-rich heterocycle. As will be discussed in more detail subsequently, non-limiting examples of substituents for various embodiments of dyes of the present teachings may include hydrogen, halogen, acid, ester, cycloakyl, alkyl, aryl, heteroaryl, arylalkyl, alkenyl, azido, alkynyl, and sulfo; alone or in combination. Such substituents by themselves be substituted by non-limiting examples such as hydrogen, halogen, alkyl, cyano, carboxylate ester, carboxamide, aryl, or heteroaryl.

One of ordinary skill in the art may recognize various assays utilizing the determination of the melting temperature ($T_m$) of a protein. The process in which a protein having, for example, a tertiary structure goes from a tertiary structure to a random coil structure is referred to in the art as, for example, but not limited by, protein denaturation, protein unfolding, and protein melt. Additionally, a protein under various sample solution conditions may show a variation or shift in the observed ($T_m$) for that protein as a function of the sample solution conditions. Various terms such as thermal melt assays (TMA), thermal shift assay (TSA), protein thermal shift (PTS) analysis, and differential scanning fluorimetry (DSF) are examples of terms of the art in which the determination of the ($T_m$) of a protein or proteins is central to the analysis.

In addition to the determination of a melting temperature ($T_m$), various embodiments of isothermal denaturation (ITD) may be utilized, in which a time to denaturation ($D_t$) is determined. For example, in some embodiments of ITD, a thermal ramp may be applied to a protein sample under a set of baseline sample solution conditions (pH, salt, ligand, etc.), and the Tm determined for those conditions. In a subsequent experiment or set of experiments, a protein sample may be subjected to various sample solution conditions. However, for the subsequent analysis, instead of a temperature ramp, the temperature determined for the baseline sample solution conditions would be used in the experiment, and the fluorescence signal would be monitored as a function of time. The experiment may be repeated at temperatures close to the predetermined ($T_m$) in order to compare the rate of denaturation as a function of time and sample solution conditions.

With respect to aspects of measurement science applied to protein chemistry, a change in detector signal amplitude may be observed as a function of the change in the folded state of a protein. In that regard, various analyses may be based on either the increase or decrease of fluorescence signal amplitude as it varies with respect to a temperature or change in temperature applied to a protein sample.

For example, in various analyses, the signal amplitude may arise from an amino acid residue of the protein, such as tryptophan. As one of ordinary skill in the art is apprised, the intensity, quantum yield, and wavelength of maximum fluorescence emission of tryptophan are very solvent dependent. The fluorescence spectrum shifts to shorter wavelength and the intensity of the fluorescence increases as the polarity of the solvent surrounding the tryptophan residue decreases. Therefore, as a protein unfolds, buried tryptophan residues may be exposed to a more polar aqueous solvent environment, so that a decreasing signal amplitude may be observed from a folded to an unfolded state.

Instead of using an intrinsic signal arising from a protein molecule, other analyses may utilize a dye to indicate a folded state of a protein. For example, a fluorescence dye, such as Sypro® Orange, may be utilized to monitor the folded state of a protein. For Sypro® Orange in a polar solvent environment, quenching of the fluorescent signal is observed. For Sypro® Orange associated with the surface groups of a folded protein in solution, the dye is in an aqueous environment, so that its fluorescence signal is quenched. As a protein is unfolded, using for example, thermal unfolding, hydrophobic regions or residues may be exposed. Sypro® Orange may then bind to hydrophobic regions or residues, and fluorescence may thereby be increased. For such a Sypro® Orange assay, then an increasing signal amplitude going from a folded to unfolded state may be observed. Dyes, such as 1-anilinonaphthalene-8-sulfonic acid (1,8-ANS) and 4,4'-Dianilino-1,1'-Binaphthyl-5,5'-Disulfonic Acid (Bis-ANS), which are quenched in aqueous environments, have been shown to be useful for monitoring protein folding, in which the fluorescence of 1,8 ANS and Bis-ANS may increase substantially in the process of, for example, protein refolding.

Monitoring protein thermal stability may be done in both academe, as well as industry for a variety reasons. For example, but not limited by, protein melt curve studies, or thermal studies, may be done for investigation of mutations to a target protein as a result of, for example, site directed mutagenesis studies. Additionally, protein thermal stability studies may be done to screen for the impact on protein stability due to a variety in vitro processing and storage conditions. Such protein thermal stability studies may screen for the impact that a variety of additives, such as, buffers, ligands, and organic agents may have on the thermal stability of the protein of interest. High throughput screening of the binding of drug candidates to protein targets may also be monitored by the impact that the binding of a drug candidate may have on protein thermal stability. Accordingly, identifying the conditions that affect protein thermal stability may enhance the identification of a variety of desired conditions impacting protein purification, crystallization, and functional characterization.

As will be discussed in more detail subsequently, various embodiments of systems and methods may utilize detector signal data collected over the entirety of a defined temperature range for a protein melt assay. According to various embodiments of methods and compositions of the present teachings, a dye according to formula (1) may be used in various analyses in which the determination of a protein ($T_m$) is desired. In such analysis, an apparatus capable of applying a controlled thermal ramp and well-controlled isothermal heating, as well as detecting the signal from a plurality of samples may be used in the determination of protein thermal melt analysis.

According to various embodiments of a thermal cycler instrument 100, as shown in FIG. 1, may be useful providing thermal control and detection for protein thermal melt analysis. A thermal cycling instrument, as depicted in FIG. 1, may include a heated cover 114 that is placed over a plurality of samples 116 contained in a sample support device. Some examples of a sample support device may include, but are not limited to, tubes, vials, and a multi-well plate permitting a selection of sample capacities, such as a standard microtiter 96-well, and 384-well plate. In various embodiments, a sample support device may be a micro device capable of processing thousands of samples per analysis, such as various microfluidic devices, microcard devices, and micro chip devices. In various embodiments, a sample support device may be a fabricated from a substantially planar support, such as a glass, metal or plastic slide, having a plurality of sample regions. The sample regions in various embodiments of a sample support device may include through-holes, depressions, indentations, and ridges, and combinations thereof, patterned in regular or irregular arrays formed on the surface of the substrate. In various embodiments, a sample support device may have a cover between the sample regions and heated cover 114. A sample support device may have sample regions arranged in a sample array format. One of ordinary skill in the art will recognize that many examples of a sample support device are patterned in row and column arrays. A sample array format according to the present teachings may include any pattern of convenient and addressable arrangement of sample regions in a sample support device, including a single row or column of sample regions in a sample support device.

In various embodiments of a thermal cycler instrument 100, include a sample block 118, an element or elements for heating and cooling and a heat exchanger 122. Various embodiments of a thermal block assembly according to the present teachings comprise components 118-122 of thermal cycler system of FIG. 1.

In FIG. 1, various embodiments of a thermal cycling system 100 have the components of embodiments of thermal cycling instrument 100 and additionally a detection system comprising, an imager 110 and optics 112. It should be noted that while a thermal cycler system is configured to detect signals from samples 116 in a sample support device during an analysis, a detection system according to the present teachings may be used to detect signals from a sample support device after an analysis has been completed.

A detection system may have an electromagnetic radiation source that emits electromagnetic energy, and a detector or imager 110, for receiving electromagnetic energy from samples 116 in sample support device. A detector or imager 110 may capable of detecting electromagnetic energy from samples 116 may a charged coupled device (CCD), backside thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and manipulation of data, for example, a computer, or other signal processing system. Additionally, optics 112 of a detection system may include components, such as, but not limited by, various positive and negative lenses, mirrors, and excitation and emission filters.

Regarding various embodiments of an electromagnetic radiation source for a detection system, such sources may include but are not limited to, white light, halogen lamps, lasers, solid state lasers, laser diodes, micro-wire lasers, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, an ensemble of LEDs, floodlight systems using LEDs, and white LEDs, filament lamps, arc lamps, gas lamps, and fluorescent tubes. Light sources can have high radiance, such as lasers, or low radiance, such as LEDs. The different types of LEDs mentioned above can have a medium to high radiance.

Multiple excitation and emission filter sets can be employed in existing thermal cycling devices, wherein each filter set may include pre-selected excitation and emission filters to provide an accurate response of signal proportional to oligonucleotide concentration in a sample at various stages of PCR. The excitation filter in a coupled set of filters can be chosen to allow wavelengths of light received from the light source that are close to the peak excitation wavelength of a predetermined dye to pass. The excitation filter can also be configured to block wavelengths of light that are greater than and less than the peak excitation wavelength. Similarly, the emission filter in the set of filters can be chosen to allow light close to the peak emission wavelength to pass while also blocking wavelengths outside the peak emission wavelength. In such a fashion, and as will be discussed in more detail subsequently, a selection of spectrally distinguishable dye species, in conjunction with the detection system, and data processing capabilities of a thermal cycling apparatus may provide for detection of a plurality of dye signals in, for example, a multiplex assay.

In use, a detection system for use with a thermal cycling device may function by impinging an excitation beam from an electromagnetic radiation source on samples in a sample support device, thereby generating a fluorescent radiation from the plurality of samples 116, Light emitted from the samples 116, may be transmitted through a lens or lenses, such as a well lens, a Fresnel lens, or a field lens, and then may be directed to additional optical components, such as a dichroic mirror, and an emission filter. Undesired wavelengths of light emitted from samples 116, may be reflected by the dichroic mirror or are blocked by the emission filter. A portion of the emitted light that transmits through the dichroic mirror and emission filter may be received by a detector or imager 110. As previously mentioned, for a thermal cycler system 100, a detector or imager may generate data signals from the fluorescent radiation from the samples over time, or may generate data signals from the fluorescent radiation from the samples at the completion of various analyses or assays. For various embodiments of systems and methods according to the present teachings, protein melt curve data is acquired over time, and a $T_m$ be determined for each sample.

Accordingly, though a thermal cycler instrument may be a useful platform for the generation and acquisition of protein melt curve data, one of ordinary skill in the art would recognize that an instrument having detection and sample thermostatting capabilities may be useful for generating protein melt curve data.

Figure 2:
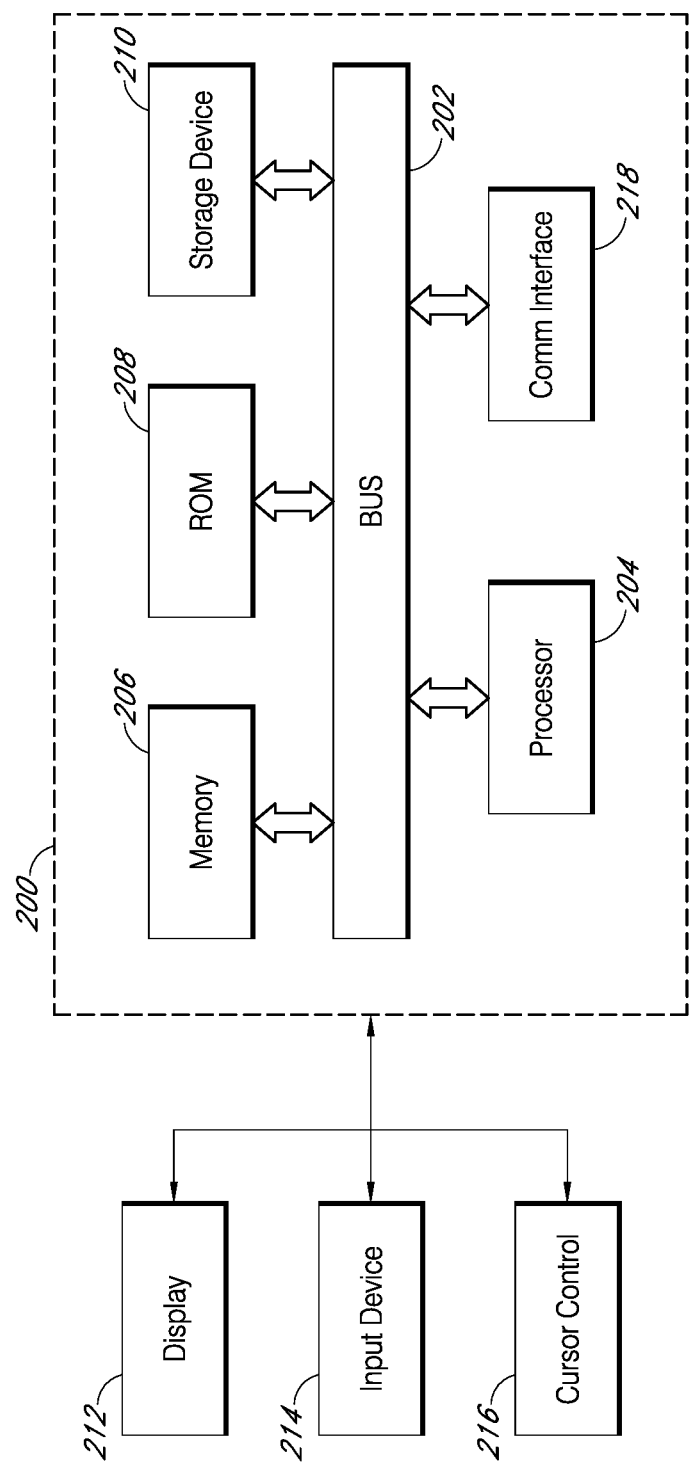
FIG. 2 is a block diagram that illustrates components of an exemplary computer system that may be utilized in the control and interface of the PCR instrumentation according to various embodiments of methods of the present teachings.

For embodiments of thermal cycler instrumentation 100, a control system 124, may be used to control the functions of the detection, heated cover, and thermal block assembly. The control system may be accessible to an end user through user interface 124 of thermal cycler instrument 100. A computer system 200, as depicted in FIG. 2 may serve as to provide the control the function of a thermal cycler instrument, as well as the user interface function. Additionally, computer system 200 may provide data processing, as well as, with other components, provide for display, and report preparation functions. For example, signals received by a detector or imager may be processed by various algorithms, such as a spectral deconvolution algorithm, which may then be displayed to an end user, as well as providing a report. All such instrument control functions may be dedicated locally to the thermal cycler instrument, or computer system 200 may provide remote control of part or all of the control, analysis, and reporting functions, as will be discussed in more detail subsequently.

FIG. 2 is a block diagram that illustrates a computer system 300, according to various embodiments, upon which embodiments of thermal cycler system 100 of FIG. 1 may utilize. Computer system 200 includes a bus 202 or other communication mechanism for communicating information, and a processor 204 coupled with bus 202 for processing information. Computer system 200 also includes a memory 206, which can be a random access memory (RAM) or other dynamic storage device, coupled to bus 202 for instructions to be executed by processor 204. Memory 206 also may be used for storing temporary variables or other intermediate information during execution of instructions to be executed by processor 204. Computer system 200 further includes a read only memory (ROM) 208 or other static storage device coupled to bus 202 for storing static information and instructions for processor 204. A storage device 210, such as a magnetic disk or optical disk, is provided and coupled to bus 202 for storing information and instructions.

Computer system 200 may be coupled via bus 202 to a display 212, such as a cathode ray tube (CRT) or liquid crystal display (LCD), for displaying information to a computer user. An input device 214, including alphanumeric and other keys, is coupled to bus 202 for communicating information and command selections to processor 204. Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (e.g., x) and a second axis (e.g., y), that allows the device to specify positions in a plane. A computer system 200 provides data processing and provides a level of confidence for such data. Consistent with certain implementations of the present teachings, data processing and confidence values are provided by computer system 200 in response to processor 204 executing one or more sequences of one or more instructions contained in memory 206. Such instructions may be read into memory 206 from another computer-readable medium, such as storage device 210. Execution of the sequences of instructions contained in memory 206 causes processor 204 to perform the process states described herein. Alternatively hard-wired circuitry may be used in place of or in combination with software instructions to implement various embodiments of methods and compositions of the present teachings. Thus implementations of the present teachings are not limited to any specific combination of hardware circuitry and software.

The term "computer-readable medium" as used herein refers to any media that participates in providing instructions to processor 204 for execution. Such a medium may take many forms, including but not limited to, non-volatile media, volatile media, and transmission media. Non-volatile media includes, for example, optical or magnetic disks, such as storage device 210. Volatile media includes dynamic memory, such as memory 206. Transmission media includes coaxial cables, copper wire, and fiber optics, including the wires that comprise bus 202. Transmission media can also take the form of acoustic or light waves, such as those generated during radio-wave and infra-red data communications. Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Further, it should be appreciated that a computer 200 of FIG. 2 may be embodied in any of a number of forms, such as a rack-mounted computer, a desktop computer, a laptop computer, or a tablet computer. According to various embodiments of a computer 200 of FIG. 2, a computer may be embedded in any number of mobile and web-based devices not generally regarded as a computer but with suitable processing capabilities. Example of such devices may include, but are not limited by a Personal Digital Assistant (PDA), a smart phone, and a notepad or any other suitable electronic device. Additionally, a computer system can include a conventional network system including a client/server environment and one or more database servers. A number of conventional network systems, including a local area network (LAN) or a wide area network (WAN), and including wireless and wired components, are known in the art. Additionally, client/server environments, database servers, and networks are well documented in the art.

As previously discussed, a dye selected from members of the family of dyes represented by formula (1) above have a number of desirable attributes that make them useful candidates as a dye for protein melt analysis. Various embodiments of a dye according to formula (1) have an excitation wavelength of between about 470 nm to about 650 nm, and an emission wavelength between about 500 nm to about 700 nm. Though not meaning to provide a complete description of the physical properties of dipyrromethenboron difluoride dyes of formula (1), the phenyl ring substituent at position 8 of the dipyrromethenboron difluoride ring structure from which the maleimide group is appended, provides for modulation of auto-fluorescence of dyes of formula (1). In that regard, it has been observed that the strongest modulation of auto-fluorescence for dyes of formula (1) may occur with the maleimide substituent is in the ortho or para position of the phenyl ring. For example, dye species (1a) and (1b) exhibit negligible background fluorescence. Moreover, with respect to the linker, Lx, the absolute length of the linker may be selected based on the impact to the modulation of the maleimide linked group to the phenyl ring. Generally, the longer the linker becomes, a decrease in modulation of the background fluorescence is expected. In that regard, a linker must be judiciously selected to optimize sufficiently low background fluorescence.

The stability of dipyrromethenboron difluoride dyes of formula (1) to a range of assay conditions provides compatibility with a range of protein melt assays. The dye has intrinsic pH stability between about pH 2 to about pH 10, which is well within a range of useful pH conditions for protein melt studies. With respect to aqueous solubility, generally, a stock solution of a dye may be prepared in a variety of polar solvents such as, but not limited by, dimethyl sulfoxide (DMSO), dimethyl formamide (DMF), acetonitrile, methanol, ethanol, and isopropanol. Once prepared in a stock solution in a polar solvent, the dyes may be prepared in a selected assay solution, which may be a buffered solution with any number of additives, for example, but not limited by, those enhancing protein stability.

As a general thumb rule, the only solution conditions that would be not favorable for the use of the dye of formula (1) for a variety of protein melt analyses would be a reactive non-protein nucleophile additive that would react with a dye and not with the intended protein target. In that regard, any of a wide variety of organic and inorganic buffers over any of a desirable range of buffer concentrations may be used with dipyrromethenboron difluoride dyes of formula (1). Additionally, a wide variety of additives, for example, but not limited by, protein stabilizing additives, may be used with dipyrromethenboron difluoride dyes of formula (1). For example, it is known that membrane proteins are generally stabilized in vitro in concentrations of surfactants at or above the critical micelle concentration (CMC). Any variety of surfactants, such as, but not limited by, the alkyl saccharide surfactants (e.g. dodecyl-β-D-maltoside (DDM); octyl-β-D-glucoside (ODG)), polysorbate surfactants (e.g. Tween 20;Tween 80), fluorinated surfactants (e.g. perfluoralkyl acids), polyoxyethylene surfactants (e.g. Brij 56;Brij 58), polyethoxylated phenol surfactants (e.g. NP-40;Triton X100), anionic surfactants (e.g. methyl ester sulfonate (MES); alcohol ether sulfate (AES)), cationic surfactants (e.g. (cetyltrimethylammonium bromide (CTAB)) and zwitterionic surfactants (e.g. CHAPS, CHAPSO, Big-CHAP), have been recognized as having properties useful for stabilizing various membrane proteins. With respect to other classes of proteins, for example, many proteins isolated from a variety of biological sources, are known to be stabilized in vitro using salts of the Hofmeister series, such as sodium chloride, potassium chloride, ammonium phosphate, and ammonium sulfate. Mono- and poly-saccharides, such as sucrose, maltose, trehalose, dextrose and sorbitol, as well as well as a number of other polyols, such as glycerol, are known to stabilize various proteins in vitro. Any of the above referenced assay conditions may be used with dipyrromethenboron difluoride dyes of formula (1) for protein melt assays.

In FIG. 3A and FIG. 3B depicts protein melt data and first derivative of the melt data, respectively, for a sample of bovine β-lactoglobulin (Sigma PN L8005). The protein was prepared in phosphate buffered saline (PBS; 137 mM NaCl, 10 mM Phosphate, 2.7 mM KCl, and a pH of 7.4) and 5% glycerol at a concentration of 3 mg/ml of protein. A 500× stock of a dye of formula (1a); BODIPY® 499/508 maleimide, was prepared at 4 mg/ml in DMSO. The dye stock solution was diluted using a protein thermal shift (PTS) phosphate buffer (250 mM, pH 7.0) to a 10× stock solution. The protein-dye reaction mixture was prepared by using 1 μl of the protein solution, 2 μl of the 10× dye solution, and 17

μl of the PTS buffer. To compare to the results obtained using BODIPY® 499/508 maleimide, β-lactoglobulin samples were prepared using Sypro® Orange. The Sypro® Orange was prepared as a 1000× stock from a 5000× stock solution in DMSO, then diluted to a 10× stock solution using the PTS buffer. The Sypro® Orange-protein reaction mixture was prepared by using 1 μl of the protein solution, 2 μl of the 10× dye solution, and 17 μl of the PTS buffer. Triplicate samples for each protein-dye mixture were run on a ViiA™ 7 qPCR instrument and analysis using Protein Thermal Shift™ software (Life Technologies Corp.). The run time conditions were: a temperature hold at 20° C. for one minute followed by a thermal ramp of 0.05° C. with continuous data collection to 95° C., followed by a 1 minute hold at the final temperature.

Figure 4A:
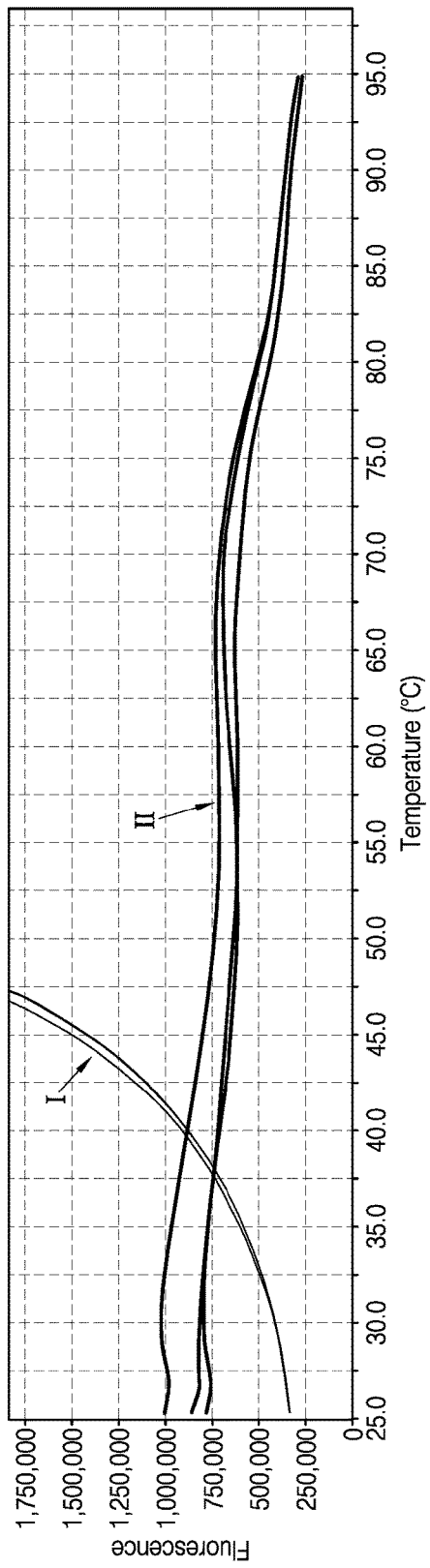
FIG. 4A is the graph of PTS data for β-lactoglobulin (bovine) shown in FIG. 3A, which is an expanded view of the details of the background for the dye known in the art of PTS.
Figure 4B:
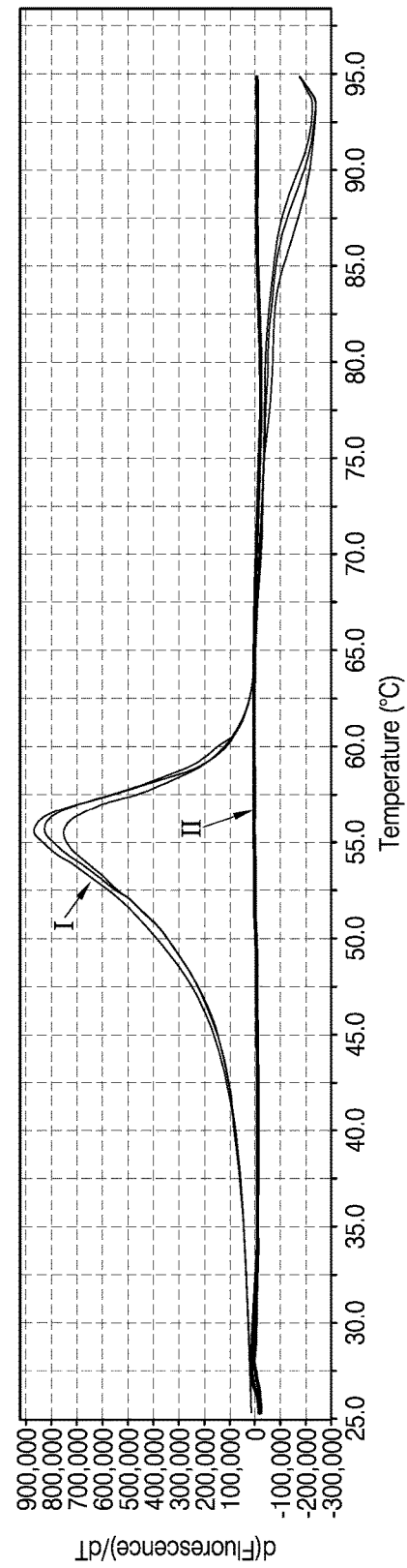
FIG. 4B depicts the first derivative graphs of the β-lactoglobulin PTS data shown for FIG. 3A.

By inspection of FIG. 3A, melt curve data for the triplicate samples using the BODIPY® 499/508 maleimide is shown in FIG. 3A-I, while the triplicate set using Sypro® Orange is shown in FIG. 3A-II shows no dye response as a function of temperature. It is clear from the data that Sypro® Orange does not work effectively with this protein to produce melt curve results. From the set of data in FIG. 3A-I, or the first derivative data shown in FIG. 3B-I, a $T_m$ of 56° C. may be determined for β-lactoglobulin. FIG. 4A is derived as blown-up section of FIG. 3A, while FIG. 4B is the same derivative data as shown in FIG. 3A. It is clear from inspection of FIG. 4A that that Sypro® Orange additionally produces a high-background. As previously mentioned, one of the attributes of dipyrrometheneboron difluoride dye of formula (1) are that they produce a negligible intrinsic background fluorescent signal. Additionally, the enhanced stability against photobleaching for dyes of formula (1) produces a clear, S-shaped curve.

Figure 5A:
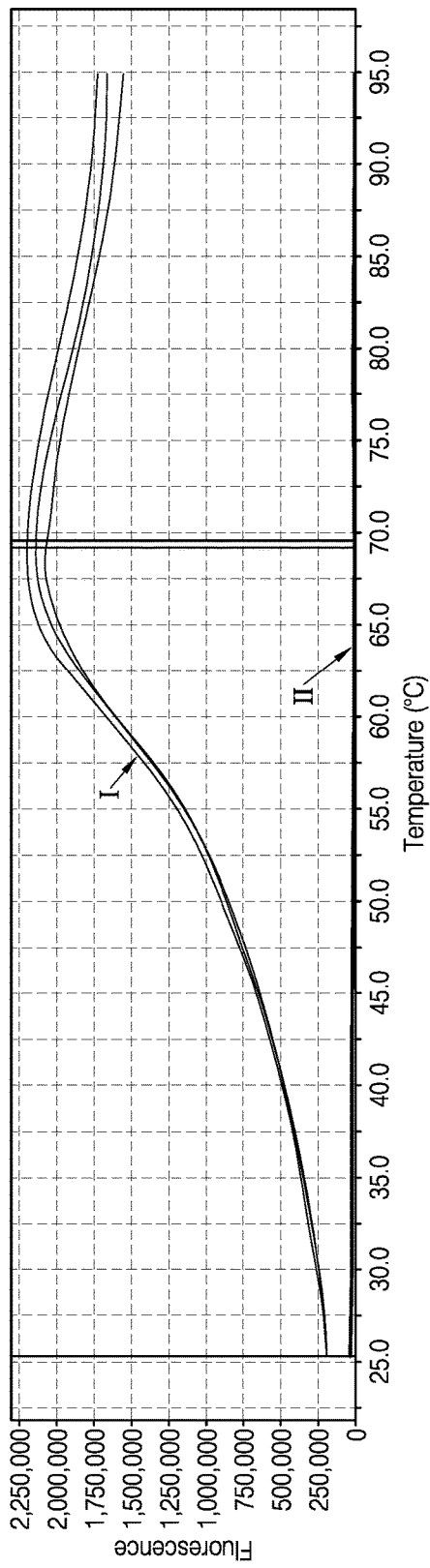
FIG. 5A is a graph of PTS data for α-chymotrypsin (bovine) using a dye according to various embodiments of systems and methods of the present teachings in comparison to dye known in the art of PTS.
Figure 5B:
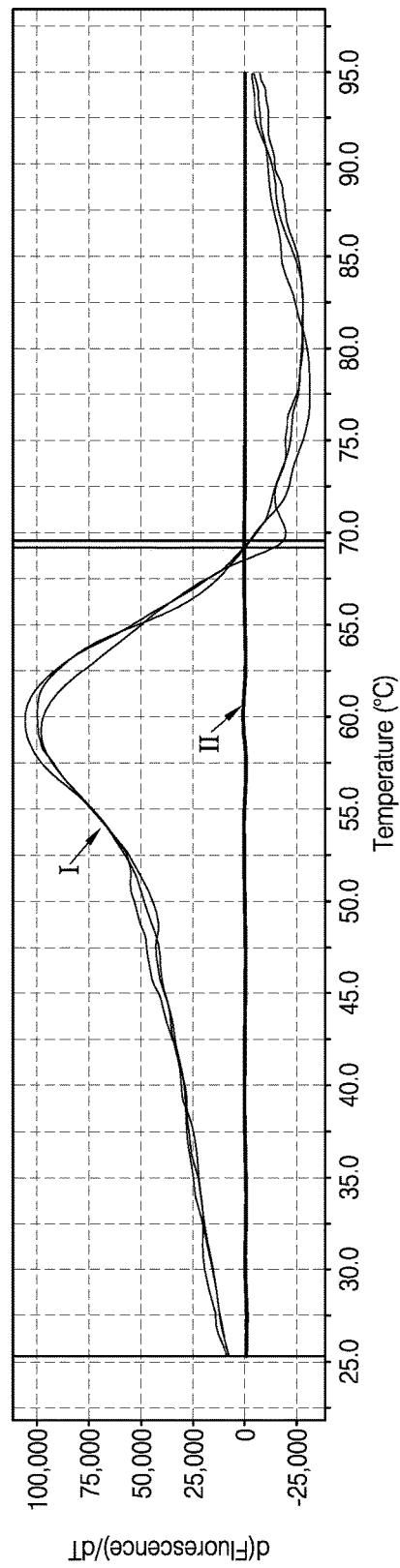
FIG. 5B shows the first derivative graphs of the α-chymotrypsin PTS data shown for FIG. 5A.

FIGS. 5A and 5B depicts protein melt data and first derivative of the melt data, respectively, for a sample of bovine α-chymotrypsin (Sigma PN C4129). Triplicate dye-protein samples for α-chymotrypsin-BODIPY® 499/508 maleimide and α-chymotrypsin-Sypro® Orange were prepared and run as described for β-lactoglobulin. As can be seen in FIG. 5A-I and FIG. 5B-II, BODIPY® 499/508 maleimide produces melt curve data, and first derivative of the melt curve data, respectively from which a $T_m$ of 59° C. may be determined for α-chymotrypsin. Similarly to the data produced for α-lactoglobulin, there are no melt curve results produced for α-chymotrypsin using Sypro® Orange. As can be seen in FIG. 6A, which is derived as blown-up section of FIG. 5A, there is no appreciable background for Sypro® Orange for this analysis.

Figure 7A:
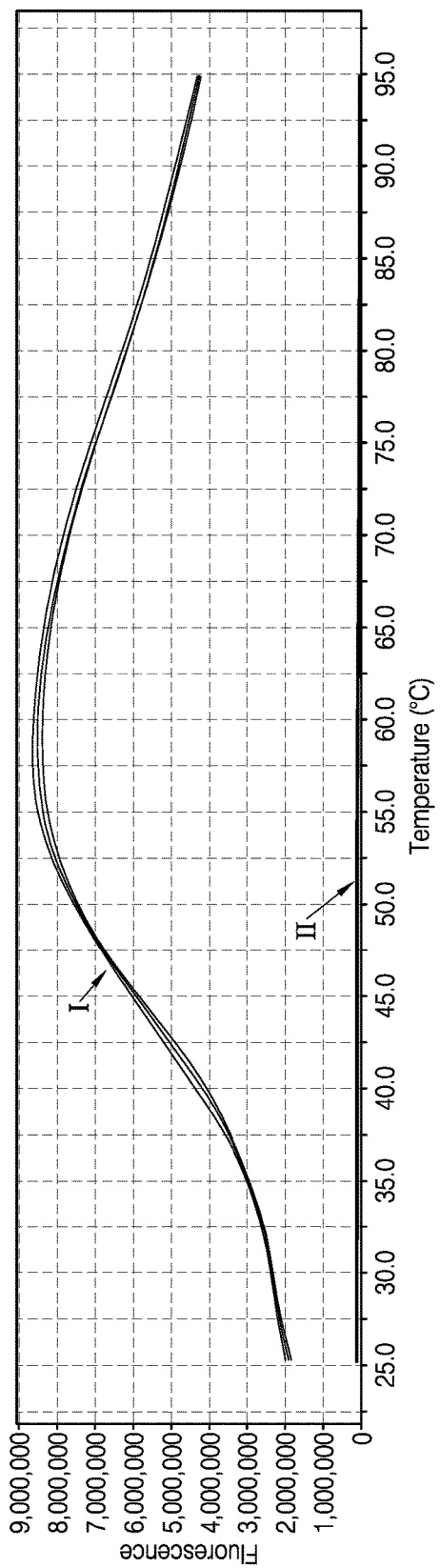
FIG. 7A is a graph of PTS data for exonuclease I (*E. coli*) using a dye according to various embodiments of systems and methods of the present teachings in comparison to dye known in the art of PTS.
Figure 7B:
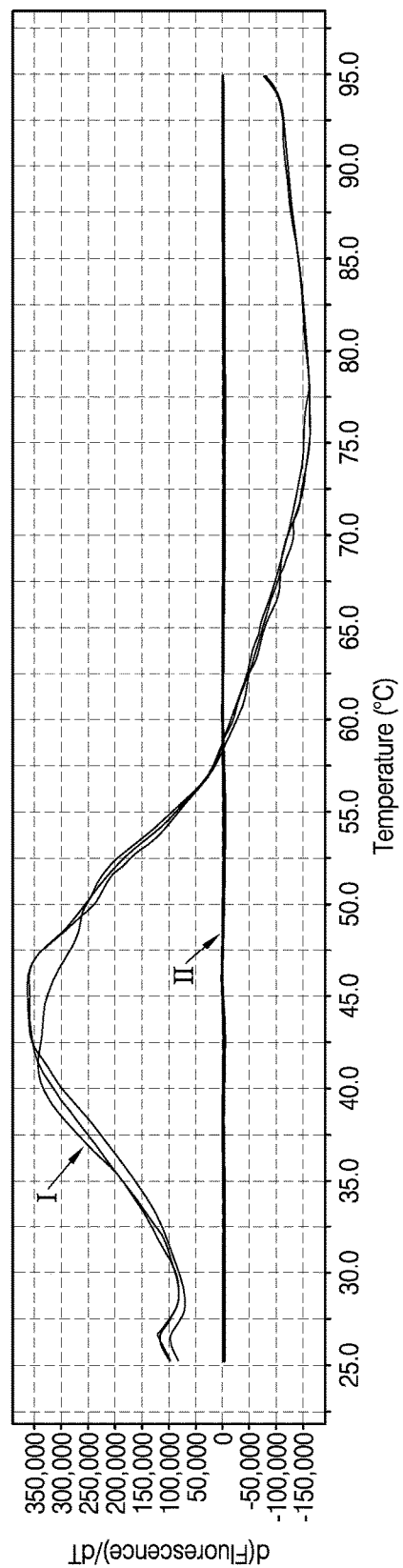
FIG. 7B shows the first derivative graphs of the exonuclease I PTS data shown for FIG. 7A.
Figure 8A:
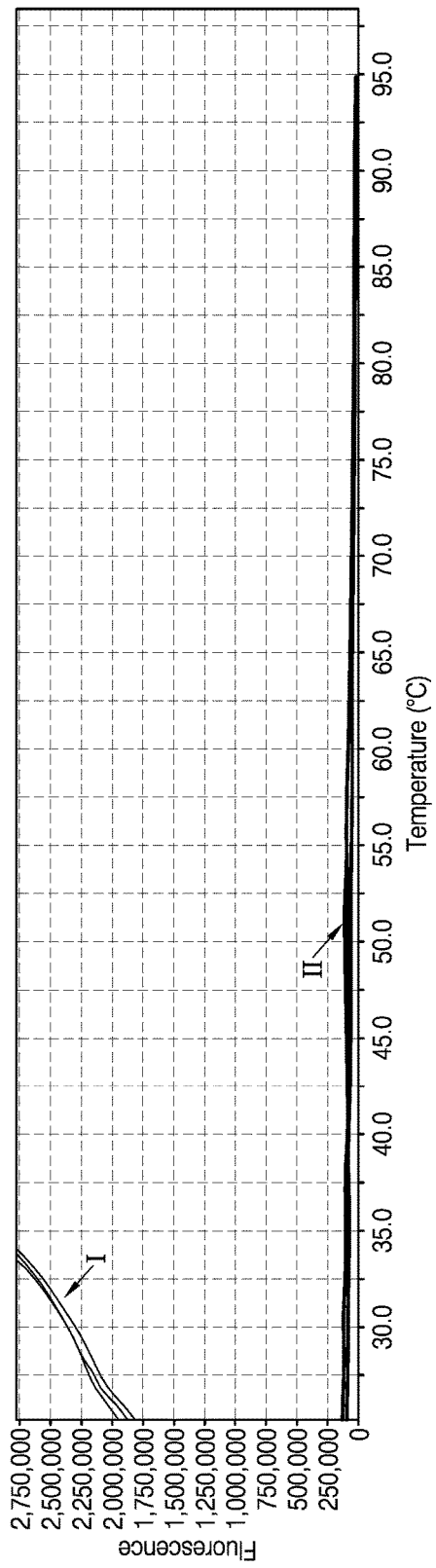
FIG. 8A is the graph of PTS data for exonuclease I (*E. coli*) shown in FIG. 7A, which is an expanded view of the details of the background for the dye known in the art of PTS.
Figure 8B:
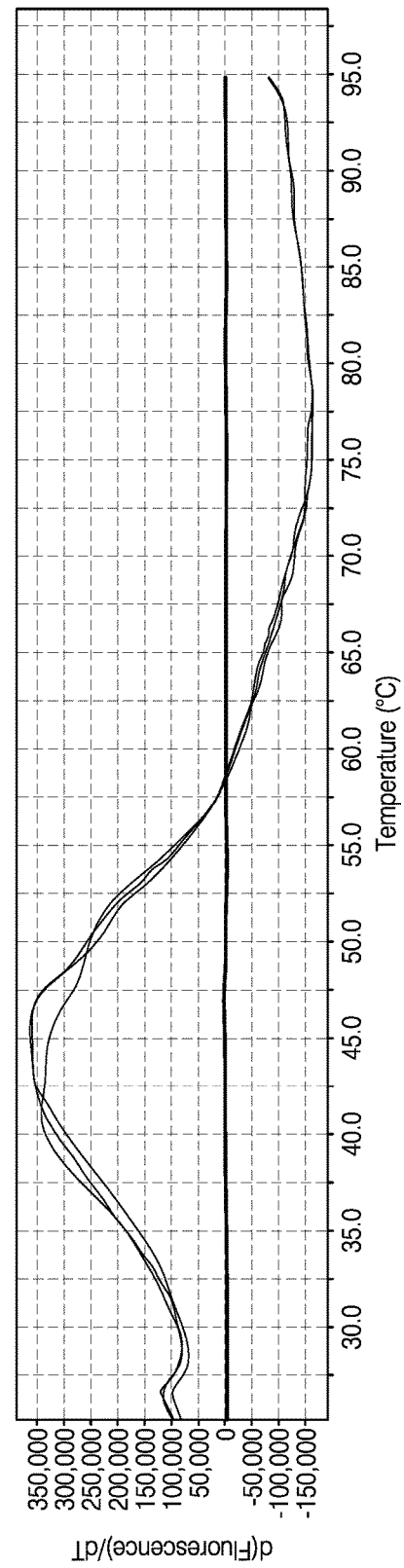
FIG. 8B depicts the first derivative graphs of the exonuclease I PTS data shown for FIG. 7A.

In FIGS. 7A and 7B an additional example of the use of BODIPY® 499/508 maleimide with a cysteine-containing protein is shown for exonuclease I. (New England Biolabs M0293L; 20 units/ul). Triplicate dye-protein samples for exonuclease I-BODIPY® 499/508 maleimide and exonuclease I-Sypro® Orange were prepared and run as described for β-lactoglobulin. As can be seen in FIG. 7A-I and FIG. 7B-II, BODIPY® 499/508 maleimide produces melt curve data, and first derivative of the melt curve data, respectively from which a $T_m$ of 40-45° C. may be determined for exonuclease I. Similarly to the data produced for α-lactoglobulin and α-chymotrypsin, there are no melt curve results produced for exonuclease I using Sypro® Orange. As can be seen in FIG. 8A, which is derived as blown-up section of FIG. 7A, there is no appreciable background for Sypro® Orange for this analysis.

Regarding FIGS. 9A and 9B, which are melt curve data and first derivative melt curve data, respectively, a sample set was run for lysozyme (Sigma L3790; 10 mg/ml), which is a protein known to have no cysteine residues. Triplicate dye-protein samples for lysozyme-BODIPY® 499/508 maleimide and lysozyme-Sypro® Orange were prepared and run as described for β-lactoglobulin. In FIG. 9A-I and FIG. 9B-I, there is no melt curve peak for the sample assayed using BODIPY® 499/508 maleimide, but an apparent peak and derivative peak in FIG. 9A-II and FIG. 9B-II for the samples run using Sypro® Orange. For the melt curve data generated using Sypro® Orange, a $T_m$ of 73° C. could be determined for lysozyme.

Figure 10A:
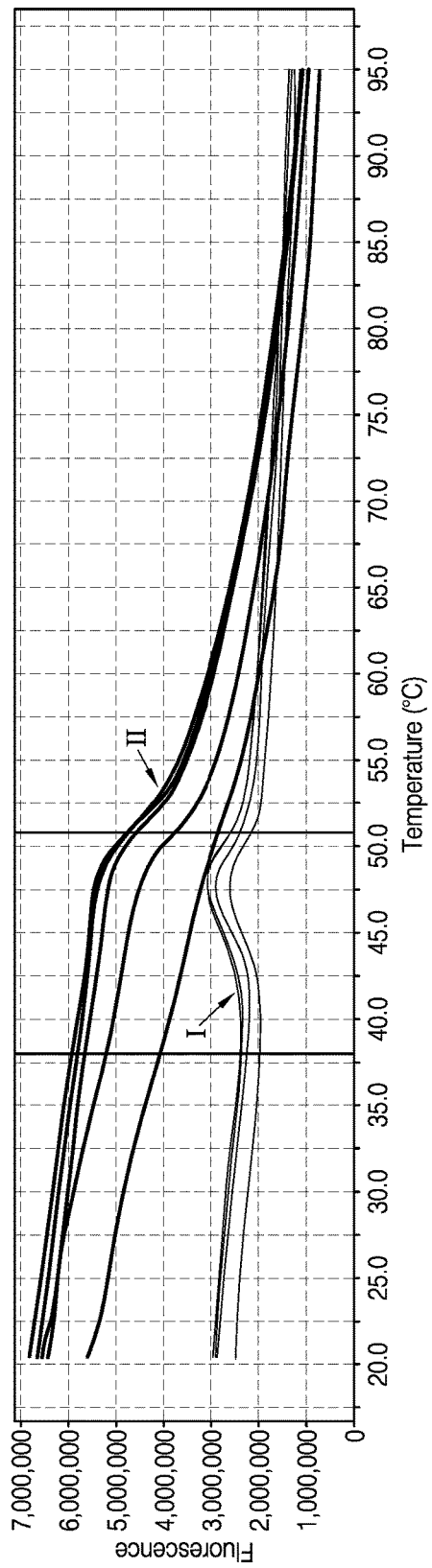
FIG. 10A is a graph of PTS data for a CAAX-containing membrane protein using a dye according to various embodiments of systems and methods of the present teachings in comparison to dye known in the art of PTS.
Figure 10B:
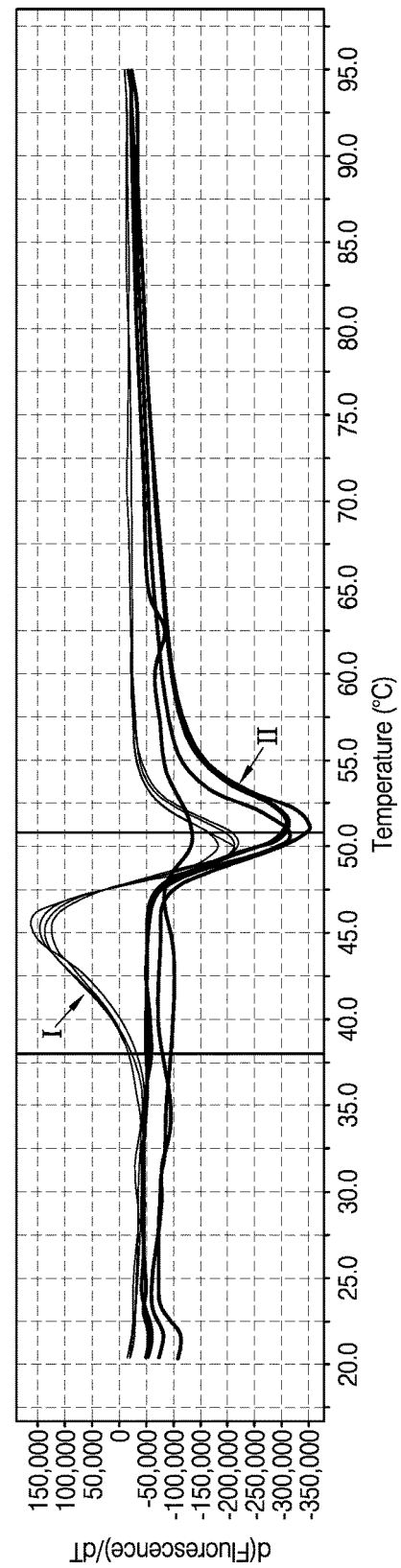
FIG. 10B shows the first derivative graphs of the CAAX-containing membrane protein PTS data shown for FIG. 10A.

Finally, FIG. 10A and FIG. 10B depict the melt curve data for a CAAX-containing membrane protein. As one of ordinary skill in the art is apprised, CAAX refers to a C-terminal prenylation signal sequence, which contains a cysteine residue. The membrane protein is suspended in a solution containing a surfactant mixture; 40 mM MES pH 6.5, 400 mM NaCl, and 0.1% DDM, in order to stabilize the membrane protein in vitro. The conditions for the assay were as previously described for β-lactoglobulin, with a total of 5 μg of the membrane protein used per assay. FIG. 10A-I and FIG. 10B-I are the protein melt data, and first derivative data, respectively for the assay run using BODIPY® 499/508 maleimide. The data indicate a $T_m$ of about 45° C. In FIG. 10A-II and FIG. 10B-II, which are the protein melt data, and first derivative data, respectively for the assay run using Sypro® Orange, there is a high sloping baseline, as well as problems with reproducibility of the replicates. The data suggest that even in the presence of high concentrations of a surfactant, that dipyrrometheneboron difluoride dye of formula (1) may give consistent results for protein melt analysis.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. The teachings should not be read as limited to the described order or elements unless stated to that effect. It should be understood that various changes in form and detail may be made without departing from the scope of the present teachings, including the order and arrangement of disclosed method steps. Therefore, all embodiments that come within the scope and spirit of the present teachings and equivalents thereto are claimed.

What is claimed is:
1. A method comprising:
   (a) forming a sample solution mixture comprising a surfactant mixture comprising an alkyl saccharide surfactant and an anionic surfactant, at least one protein and a dye of formula (I):

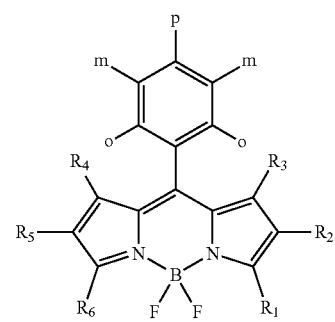

wherein:
R$_1$ to R$_6$ is independently selected from the group consisting of: hydrogen, halogen, —(CH$_2$)$_n$CO$_2$H, wherein n=0 to 6, —(CH$_2$)$_n$CO$_2$R, wherein n=0 to 6, cycloakyl, alkyl, wherein the alkyl has 1-5 carbon atoms, aryl, heteroaryl, arylalkyl, wherein the alkyl portion has 1-5 carbon atoms, alkenyl, azido, alkynyl, and sulfo, alone or in combination,
wherein o, m and p are independently selected from the group consisting of: hydrogen, halogen, —(CH$_2$)$_n$CO$_2$H, wherein n=0 to 6, —(CH$_2$)$_n$CO$_2$R, wherein n=0 to 6, cycloakyl, alkyl, wherein the alkyl has 1-5 carbon atoms, aryl, heteroaryl, arylalkyl, wherein the alkyl portion has 1-5 carbon atoms, alkenyl, azido, alkynyl, sulfo, and a maleimidyl substituent having the structure:

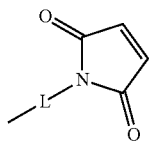

alone or in combination, with the provisio that the maleimidyl substituent occurs in formula (I) once and only once,
wherein an alkenyl substituent is substituted or unsubstituted,
wherein the alkenyl group is ethenyl, dienyl, or trienyl,
wherein the one or more substituents for an alkenyl group is selected from the group consisting of: hydrogen, halogen, alkyl, wherein the alkyl has 1-5 carbon atoms, cyano, carboxylate ester, carboxamide, aryl, heteroaryl, and any combination thereof,
wherein an aryl is selected from phenyl, 1-naphthyl, 2-naphthyl, 1-pyrenyl, 9-anthryl, pyridyl, quinolyl, and alkoxy derivatives thereof,
wherein an aryl or heteroaryl group is substituted or unsubstituted,
wherein the one or more substituents for an aryl or heteroaryl group is selected from the group consisting of: hydrogen, halogen, —(CH$_2$)$_n$CO$_2$H, wherein n=0 to 6, —(CH$_2$)$_n$CO$_2$R, wherein n=0 to 6, alkyl, wherein the alkyl has 1-5 carbon atoms, alkoxy, wherein the alkyl portion has 1-4 carbon atoms, and any combination thereof,
wherein any alkyl or arylalkyl group is substituted or unsubstituted,
wherein the one or more substituents for an alkyl or arylalkyl group is selected from the group consisting of: hydrogen, halogen, —(CH$_2$)$_n$CO$_2$H, wherein n=0 to 6, —(CH$_2$)$_n$CO$_2$R, wherein n=0 to 6, cycloakyl, alkyl, wherein the alkyl has 1-5 carbon atoms, aryl, heteroaryl, arylalkyl, wherein the alkyl portion has 1-5 carbon atoms, alkenyl, azido, alkynyl, and sulfo, alone or in combination,
wherein the alkyl group in any substituent of an aryl group may be further substituted by an ester or amide substituent, and
wherein L is an optionally present linker and when present L is selected from alkyl, wherein the alkyl has 1-6 carbon atoms, and heteroalkyl, wherein the heteroalkyl has 1-6 atoms; and
(b) applying a controlled heating to the mixture; and
(c) measuring fluorescence emitted over a temperature range.

2. The method of claim 1, wherein the dye in the sample solution mixture is 4,4-difluoro-1,3,5,7-tetramethyl-8-(4-maleimidylphenyl)-4-bora-3a,4a-diaza-s-indacene.

3. The method of claim 1, wherein the dye in the sample solution mixture is 4,4-difluoro-3,5-bis(4-methoxyphenyl)-8-(4-maleimidylphenyl)-4-bora-3a,4a-diaza-s-indacene.

4. The method of claim 1, wherein the controlled heating is a thermal ramp.

5. The method of claim 4, wherein the thermal ramp is between about 20° C. to about 95° C.

6. The method of claim 1, wherein the controlled heating is isothermal heating.

7. The method of claim 1, wherein the surfactant mixture further comprises a buffer.

8. The method of claim 1, wherein the alkyl saccharide surfactant and the anionic surfactant are at or above the critical micelle concentration.

9. The method of claim 1, wherein the surfactant mixture further comprises a polyol.

10. The method of claim 9, wherein the polyol is glycerol.

11. The method of claim 9, wherein the polyol is a polysaccharide.

12. The method of claim 1, wherein the alkyl saccharide surfactant is selected from the group consisting of dodecyl-β-D-maltoside (DDM) and octyl-β-D-glucoside (ODG).

13. The method of claim 1, wherein the anionic surfactant is selected from the group consisting of methyl ester sulfonate (MES) and alcohol ether sulfate (AES).

* * * * *